US012788169B2

(12) United States Patent
Blake

(10) Patent No.: US 12,788,169 B2
(45) Date of Patent: Nov. 10, 2026

(54) SLEEVE FOR DONNING GARMENT ON RESIDUAL LIMB

(71) Applicant: United States Government as represented by the Department of Veterans Affairs, Washington, DC (US)

(72) Inventor: Jason Blake, Concord Township, OH (US)

(73) Assignee: United States Government as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 19/003,272

(22) Filed: Dec. 27, 2024

(65) Prior Publication Data

US 2026/0114649 A1 Apr. 30, 2026

Related U.S. Application Data

(60) Provisional application No. 63/615,007, filed on Dec. 27, 2023.

(51) Int. Cl.
*A47G 25/90* (2006.01)
*A61F 2/78* (2006.01)

(52) U.S. Cl.
CPC ...... *A47G 25/90* (2013.01); *A61F 2002/7825* (2013.01)

(58) Field of Classification Search
CPC .... A47G 25/90; A47G 25/905; A47G 25/907; A41D 13/0543; A41D 13/08; A41D 13/065; A61F 2/78; A61F 2/7812; A61F 2002/7818; A61F 2002/7825; A61F 2002/7831; A61F 2002/7837
See application file for complete search history.

(56) References Cited

U.S. PATENT DOCUMENTS

| | | | | | |
|---|---|---|---|---|---|
| 397,752 | A * | 2/1889 | Ready | A47G 25/905 | 223/111 |
| 6,327,710 | B1 * | 12/2001 | Dunn | A41D 13/0543 | 2/22 |
| 7,699,195 | B2 * | 4/2010 | Scott | A47G 25/907 | 223/111 |
| 10,238,225 | B2 * | 3/2019 | Asher | A47G 25/905 | |
| 12,161,571 | B2 * | 12/2024 | Astilla | A61F 2/78 | |
| 12,310,865 | B2 * | 5/2025 | Stevenson | A61F 2/7812 | |
| 2005/0241046 | A1 * | 11/2005 | Griesbach, III | A41D 19/0041 | 2/160 |
| 2009/0242594 | A1 * | 10/2009 | Van Den Berge | A47G 25/907 | 223/111 |
| 2010/0089954 | A1 * | 4/2010 | Rondeau | A47G 25/907 | 223/111 |
| 2023/0372127 | A1 * | 11/2023 | Layman | A61F 2/78 | |

* cited by examiner

*Primary Examiner* — F Griffin Hall
(74) *Attorney, Agent, or Firm* — Ballard Spahr LLP

(57) ABSTRACT

An apparatus for donning a garment over a residual limb is disclosed. The apparatus includes a sleeve having a first end and a second end spaced along a longitudinal axis. The sleeve has a peripheral sidewall surrounding the longitudinal axis. An opening is defined by the peripheral sidewall and extends continuously through the sleeve from the first end to the second end. At least one series of perforations extending from the first end to the second end of the sleeve.

18 Claims, 6 Drawing Sheets

SLEEVE FOR DONNING GARMENT ON RESIDUAL LIMB

CROSS-REFERENCE TO RELATED APPLICATIONS

This application claims priority to and the benefit of the filing date of U.S. Provisional Patent Application No. 63/615,007, filed Dec. 27, 2023, the entirety of which is hereby incorporated by reference herein.

FIELD

This application relates to devices and methods for donning garments on limbs, such as, for example, donning a compression stocking on a residual limb.

BACKGROUND

Individuals with residual limbs, such as, for example, partial leg amputations, often use prosthetic limbs. Typically, a stocking is positioned over the residual limb, and the prosthesis is positioned over the stocking.

Difficulties can arise as the stocking is pulled over the residual limb. Further, the stocking is often a compression stocking. For example, in order for the stocking to fit properly under the prosthesis, the stocking can be tight-fitting. Accordingly, pulling the stocking over the residual limb can be difficult. Further, particularly in the case of recent amputation, the residual limb can have delicate tissue that can tear during donning of the stocking. Residual limbs from recent amputations present distinct challenges arising from the fragility of the skin and the possible presence of biological fluids, including blood and plasma.

Further, individuals such as elderly individuals wear compression garments such as compression socks. It can be difficult for certain individuals to don such compression garments, particularly when said individuals have limited grip strength.

Accordingly, an improved way of donning a garment over a limb/residual limb is desirable.

SUMMARY

Disclosed herein, in one aspect, is an apparatus for donning a garment over a residual limb. The apparatus includes a sleeve having a first end and a second end spaced along a longitudinal axis. The sleeve has a peripheral sidewall surrounding the longitudinal axis. An opening is defined by the peripheral sidewall and extends continuously through the sleeve from the first end to the second end. At least one series of perforations extending from the first end to the second end of the sleeve.

Additional advantages of the disclosed system and method will be set forth in part in the description which follows, and in part will be understood from the description, or may be learned by practice of the disclosed system and method. The advantages of the disclosed system and method will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed apparatus, system, and method and together with the description, serve to explain the principles of the disclosed apparatus, system, and method.

DETAILED DESCRIPTION

Figure 1:
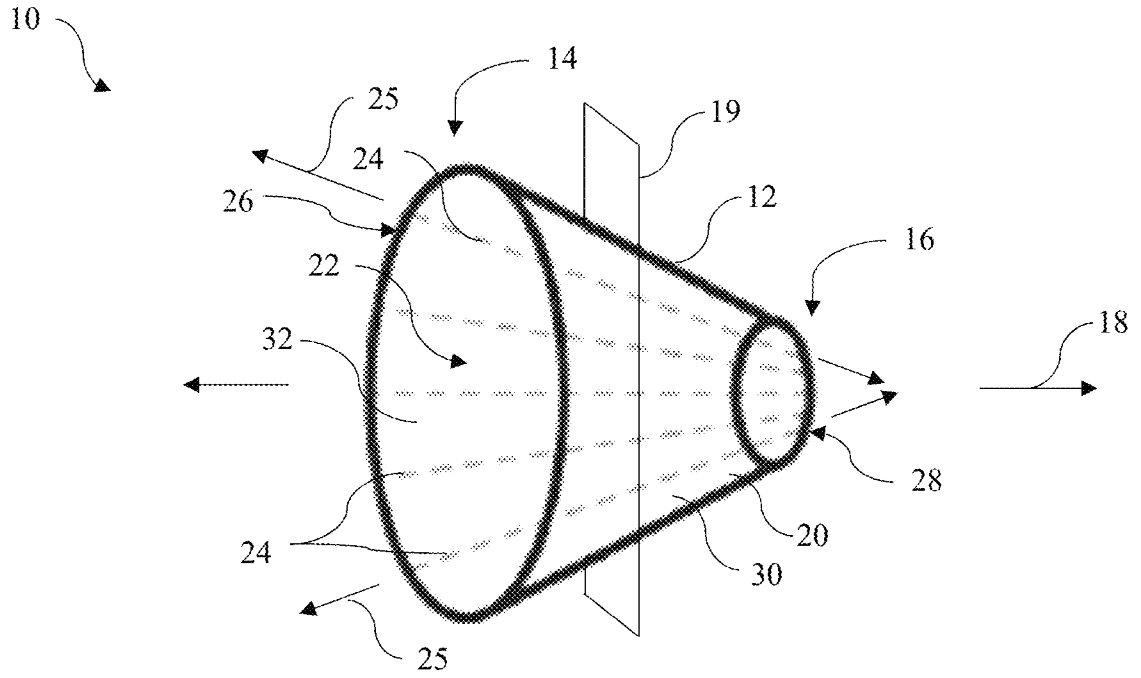
FIG. 1 is a perspective view of an exemplary apparatus for donning a garment over a residual limb as disclosed herein.

The disclosed system and method may be understood more readily by reference to the following detailed description of particular embodiments and the examples included therein and to the Figures and their previous and following description.

It is to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" can include plural references unless the context clearly dictates otherwise. Thus, for example, reference to "a kit" amounts to a disclosure of embodiments in which only a single kit is provided, as well as embodiments in which a plurality of kits are provided.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Optionally, in some aspects, when values or characteristics are approximated by use of the antecedents "about," "substantially," or "generally," it is contemplated that values within up to 15%, up to 10%, up to 5%, or up to 1% (above or below) of the particularly stated value or characteristic can be included within the scope of those aspects.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Referring now to FIGS. 1-6, an apparatus 10 for donning a garment [80] over a residual limb can comprise a sleeve 12 having a first end 14 and a second end 16 spaced along a longitudinal axis 18. The sleeve 12 can have a peripheral sidewall 20 surrounding the longitudinal axis 18. The peripheral side wall 20 can define an opening 22 that extends continuously through the sleeve 12 from the first end 14 to the second end 16. The sleeve 12 can have at least one series of perforations 24 extending from the first end 14 to the second end 16 of the sleeve 12. The at least one series of perforations 24 can be configured to permit tearing of the sleeve 12 from the first end 14 to the second end 16.

The peripheral wall 20 can have a first edge 26 at the first end 14 and a second edge 28 at the second end 16 of the sleeve 12. The first edge 26 can surround the opening 22 of the sleeve at the first end, and the second edge 18 can surround the opening 22 at the second end 16.

Figure 4:
FIG. 4 is an end view of the apparatus of FIG. 1 is a flattened configuration.

In some aspects, the sleeve 12 can define a taper between the first end 14 and the second end 16. Optionally, in these aspects, the taper can extend continuously from the first end to the second end. The taper can optionally be linear. In other aspects, the degree of taper can change along the length of the sleeve 12. In exemplary aspects, the perforations of each respective series of perforations 24 can be aligned along an axis 25 that follows the taper of the sleeve 12. In some aspects, the axis 25 of at least one (optionally, all) of the series of perforations 25 can follow a shortest path from a respective starting location on the first edge 26 to the second edge 28. For example, the axis 25 can follow a path of the longitudinal axis 18 (extending through a center point of the sleeve projected radially outwardly against the sleeve). In additional aspects, when the sleeve 12 is flattened (as shown in FIG. 4), each series of perforations can extend parallel or substantially parallel (e.g., within 10 degrees of parallel) to the longitudinal axis 18. In exemplary aspects, each perforation of the series of perforations can be elongate along the respective axis 25. Connecting portions of the sleeve can be positioned between sequential perforations of the series of perforations. In some aspects, the perforations can be longer than the connecting portions along the axis 25. In some exemplary aspects, the perforations can be formed with a pinwheel. In other aspects, the perforations can be formed with a press or using any other suitable method.

Figure 5:
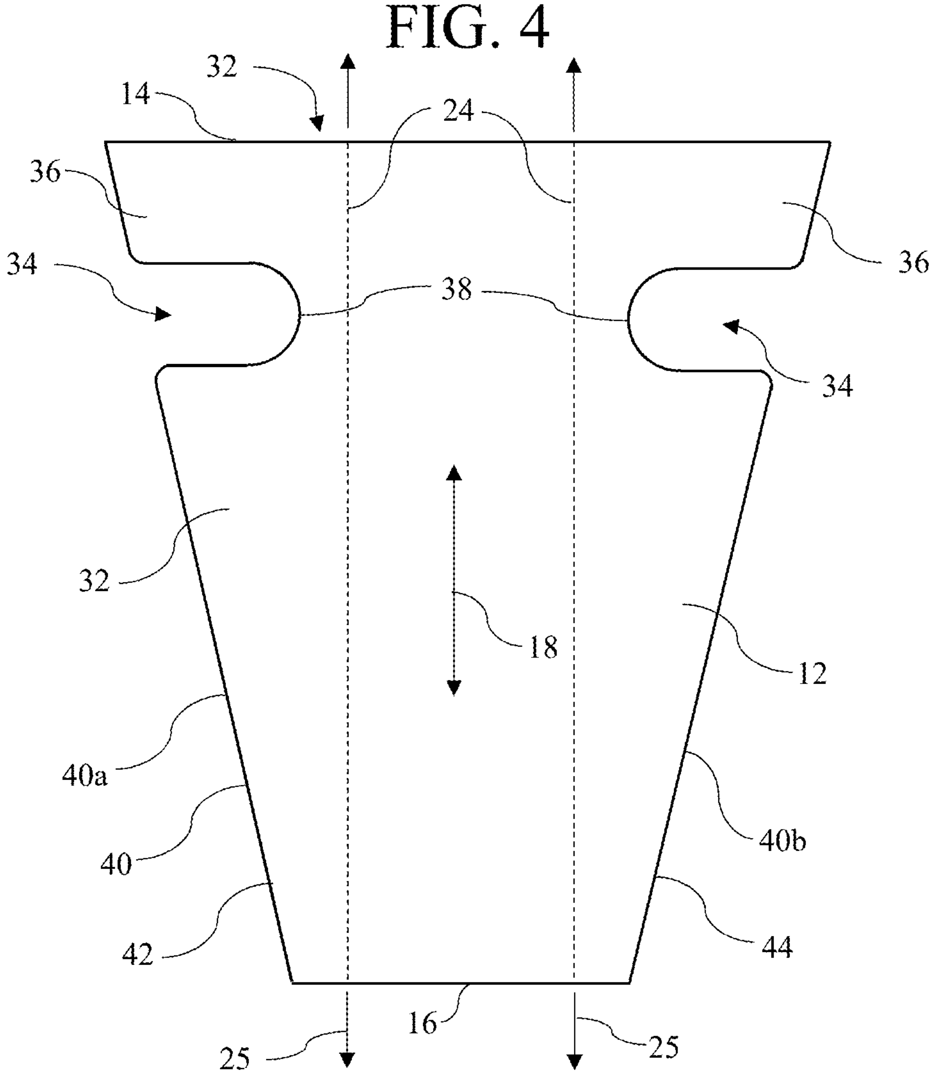
FIG. 5 is a side view of an exemplary apparatus as disclosed herein.
Figure 6:
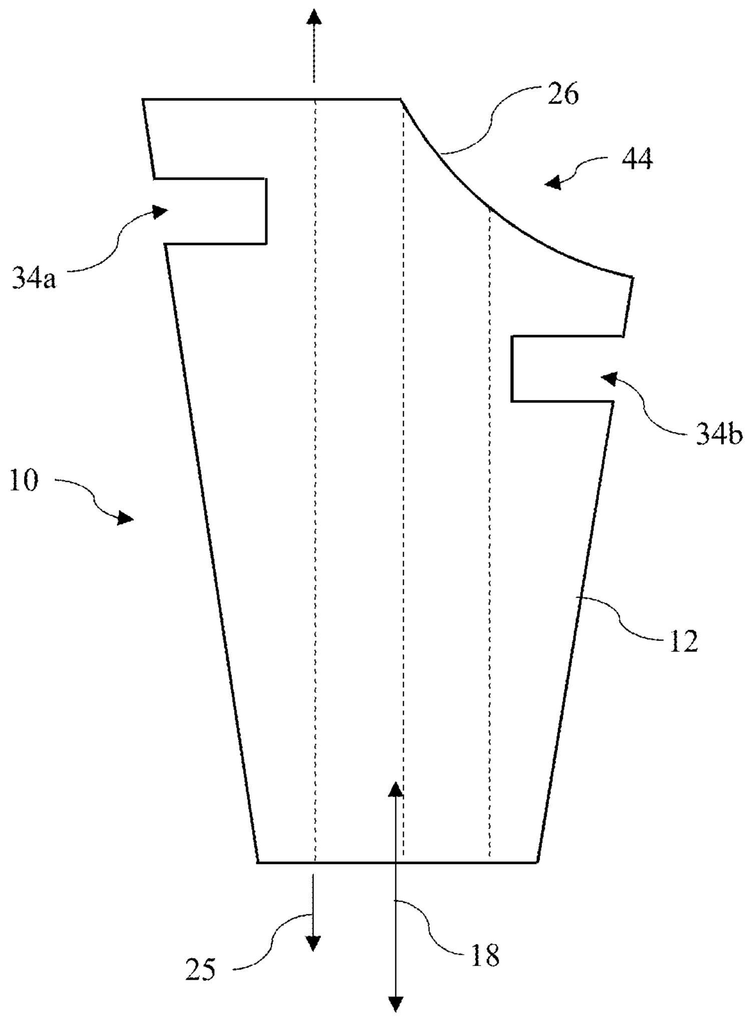
FIG. 6 is a side view of an exemplary apparatus as disclosed herein.

The peripheral sidewall 20 of the sleeve 12 has an outer surface 30 and an inner surface 32. Referring to FIGS. 5-6, in some aspects, the sleeve 12 can define at least one transverse opening 34 extending through the peripheral sidewall 20 of the sleeve 12 from the outer surface 30 to the inner surface 32. The at least one transverse opening 34 can be sized to receive one or a plurality of fingers therethrough. In some aspects, the at least one transverse opening 34 can be elongated along a transverse axis that is perpendicular or substantially perpendicular (e.g., within 10 degrees of perpendicular) to the longitudinal axis. For example, the at least one transverse opening 34 can receive four fingers of the user so that the portion of the sleeve 12 between the at least one transverse opening 34 and the first opening serves as a handle 36 for pulling the sleeve over the residual limb. Accordingly, in some optional aspects, the at least one transverse opening 34 can have a major dimension of at least 2 or at least 3 inches or between 2 inches and 8 inches. In other aspects, the at least one transverse opening 34 can comprise a plurality of openings positioned relative to each other to receive respective fingers of one hand therethrough. In some aspects, the at least one transverse opening can be positioned closer to the first end 14 of the sleeve 12 than to the second end 16 of the sleeve. In some aspects, the transverse openings 34 can have arcuate edges to reduce stresses that lead to undesired tearing.

In some aspects, the at least one series of perforations 24 can be spaced from lateral edges 38 of the at least one transverse opening 34 (e.g., by at least ½ inch or at least one inch). In this way, inadvertent tearing of the sleeve 12 can be avoided as the handle 36 is being used.

In some aspects, the sleeve 12 can be unitarily formed. In some aspects, the sleeve 12 can have at least one longitudinal weld 40 (e.g., a heat weld) extending from the first end 14 to the second end 16. For example, the at least one longitudinal weld 40 can comprise a first longitudinal weld 40*a* on a first side 42 of the sleeve 12 and a second longitudinal weld 40*b* on a second side 44 of the sleeve. In other aspects, the sleeve 12 can comprise a single longitudinal weld 40. For example, the sleeve 12 can comprise a rolled material. In exemplary aspects, the at least one longitudinal weld 40 can secure respective portions (e.g., overlapping edge portions) of a rolled material together to form the sleeve.

In some aspects, at least a portion of the first edge 26 can define a cutout 44 extending toward the second end of the sleeve. The cutout 44 can be received along an inner thigh of the user to permit a portion of the sleeve 12 on a side opposite the cutout to extend past the user's groin area. Optionally, in these aspects, a first transverse opening 34*a* can be longitudinally offset from a second transverse opening 34*b*.

Figure 2:
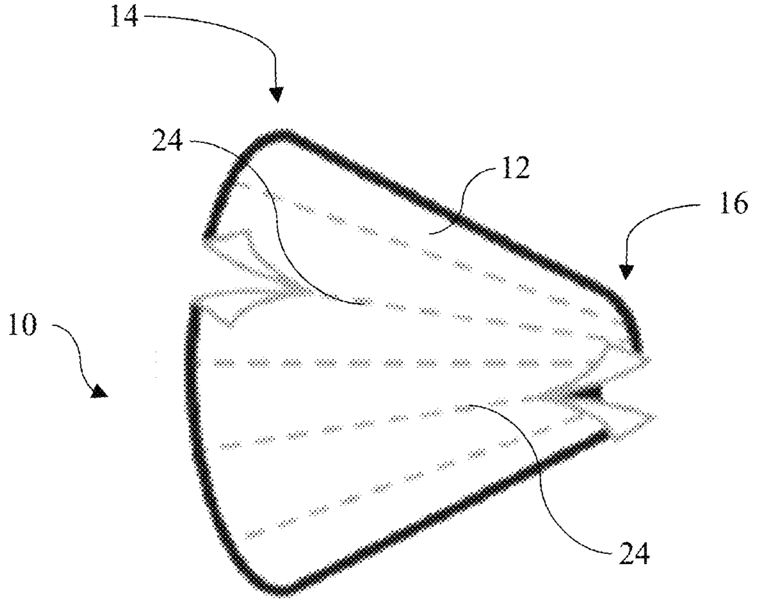
FIG. 2 is a perspective view of the apparatus of FIG. 1 being torn along two series of perforations.
Figure 3:
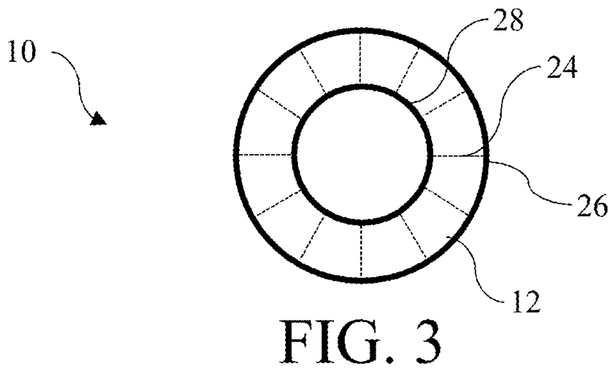
FIG. 3 is an end view of the apparatus of FIG. 1.

In some aspects, the sleeve 12 can comprise polymer. For example, the sleeve 12 can comprise polyethylene. In further aspects, the sleeve 12 can comprise polypropylene, polystyrene, Polyethylene terephthalate (PET), or any suitable material. More generally, the sleeve 12 can comprise a polymer that provides a surface against which a garment such as a stocking slides. In some aspects, the sleeve 12 can be made of recyclable polymer. Optionally, the sleeve 12 can comprise a coating to promote sliding of the garment along the outer surface. The sleeve 12 can be flexible to conform to the shape of the residual limb. Further, the sleeve 12 can be configured to stretch to accommodate the residual limb. Additionally, the sleeve 12 can be flexibly movable about and between a compact configuration (e.g., a flattened configuration, shown in FIG. 4, or in a folded configuration) and an expanded use configuration (FIGS. 1-3).

In some optional aspects, the peripheral side wall 20 of the sleeve 12 can have a thickness of 3 mils (thousandths of an inch) or less. For example, the peripheral side wall 20 can have a thickness from about 0.5 mils to about 3 mils, or from about 1 mil to about 2 mils, or from 0.5 mils to 2 mils, or from 1 mil to 3 mils. It is further contemplated that the sleeve can have a thickness of greater than 3 mils (e.g., from about 3 mils to about 5 mils).

Figure 11:
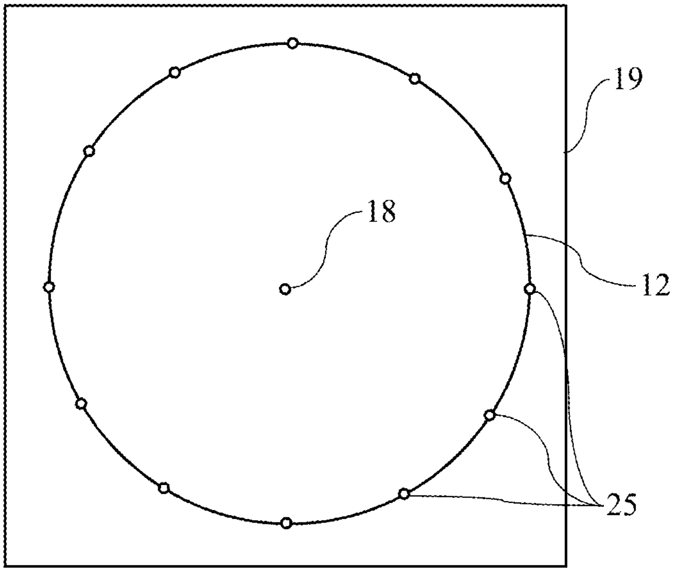
FIG. 11 is a schematic drawing of a cross sectional plane extending perpendicular to centrally positioned longitudinal axis of the apparatus, showing respective locations of axes of series of perforations relative to each other.

In some aspects, the at least one series of perforations 24 can comprise a plurality of series of perforations, with the respective series of perforations (e.g., the respective axes 25 along which the perforations of a respective series of perforations are aligned) being circumferentially spaced from one another about an outer surface 30 of the peripheral sidewall 20. In some aspects, the plurality of series of perforations 24 can be evenly circumferentially spaced about the outer surface of the peripheral sidewall (such that a circumferential spacing between sequential series of perforations is consistent throughout the entire circumference of the sleeve). Optionally, in exemplary aspects, and with reference to FIG. 11, when the longitudinal axis 18 extends through a center point of the sleeve, it is contemplated that within planes 19 that are perpendicular to the longitudinal axis, the respective axes 25 along which perforations of each respective series of perforations are aligned can be equally or substantially equally radially spaced from the longitudinal axis. In other aspects, the plurality of series of perforations 24 can be unevenly circumferentially spaced about the outer surface of the peripheral sidewall (such that a circumferential spacing between at least two sequential series of perforations is different than a circumferential spacing between at least two other sequential series of perforations). In various aspects, the plurality of series of perforations 24 can comprise from two to 15 series of perforations, or from four to ten series of perforations.

The opening 22 defined by the sleeve 12 can be configured to receive at least a portion of the residual limb therein. Accordingly, the dimensions of the sleeve 12 can be selected for receipt of the residual limb. It is contemplated that the sleeve 12 can be sized for different amputation locations (e.g., below-the-knee, at-the-knee, or above-the-knee) or for different leg sizes (e.g., small, medium, large). For an above-the-knee amputation, the first end 14 of the sleeve 12 can have a dimension (e.g., diameter) sufficient to receive a portion of a thigh. For example, in an exemplary embodiment of the apparatus 10, the first end 14 can be sized to receive a thigh having a circumference of up to 25 inches. In additional aspects, the sleeve 12 can taper so that the second end 16 is configured to receive a portion of a residual limb having a circumference of 16 inches. It is contemplated that a sleeve 12 having a first end 14 configured to receive a residual limb having a circumference of up to 25 inches and tapering so that the second end 16 is configured to fit snugly against a portion of the residual limb having a circumference of 16 inches can suitably fit different individuals having a residual limb with dimensions within the range of 16 inches to 25 inches. For example, the sleeve 12 can be pulled up the residual limb until the second end 16 snugly engages the limb. The sleeve 12 can be suitably sized if the second end 16 snugly engages the limb (e.g., resisting further movement) and a portion of the sleeve extends sufficiently along the residual limb to facilitate sliding of the garment therealong. In various exemplary aspects, the first end 14 can be sized to receive a limb having a circumference of up to 32 inches. In another aspect, the first end 14 can be sized to receive a limb having a circumference of up to 22 inches. In another aspect, the first end 14 can be sized to receive a limb having a circumference of up to 18 inches. In various aspects, the second end 16 is configured to receive a residual limb with a circumference of 12 inches, or 14 inches, or 16 inches, or 18 inches. In some aspects, the sleeve 12 can have a length along the longitudinal axis between the first end 14 and the second end 16 from about 8 inches to about 30 inches, or about 8 inches to about 24 inches, or from about 12 inches to about 18 inches. More generally, the sleeve 12 can have any suitable length and circumferential dimensions at the first and second ends 14, 16. For example, in additional aspects, the apparatus 10 can be sized for children. In further aspects, the apparatus 10 can be sized for use in donning a garment such as a compression sleeve over an arm. Accordingly, the apparatus can have dimensions for receiving an arm. In further aspects, the apparatus 10 can be sized for positioning a garment such as a compression sock over a foot of a user.

Figure 7:
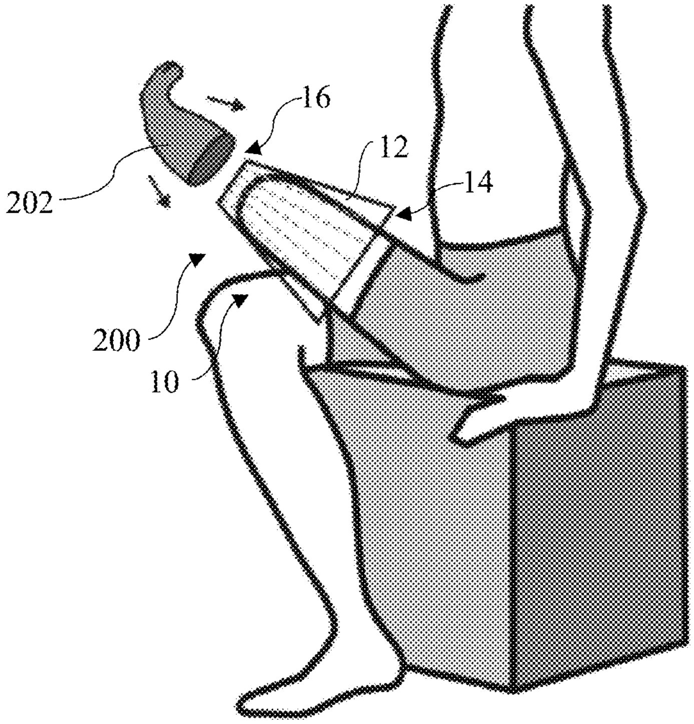
FIG. 7 is a schematic drawing showing use of the apparatus to don a stocking on the residual limb.
Figure 8:
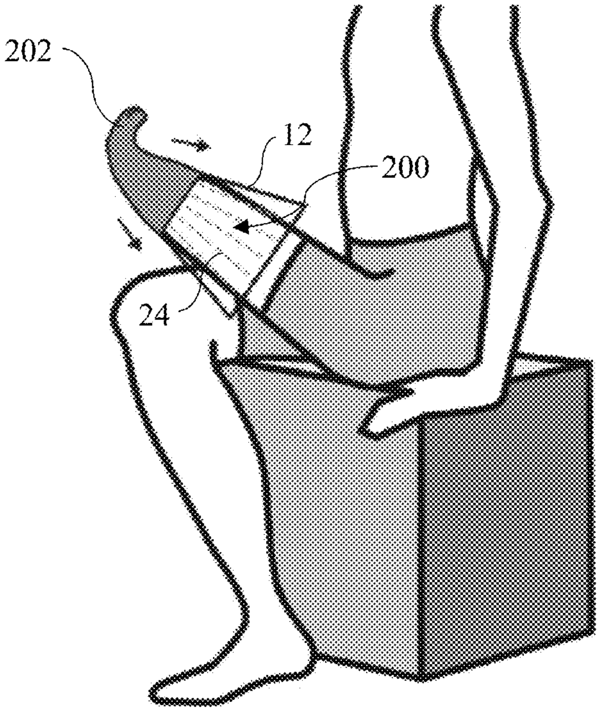
FIG. 8 is a schematic drawing showing another stage of donning of the stocking following that in FIG. 7.
Figure 9:
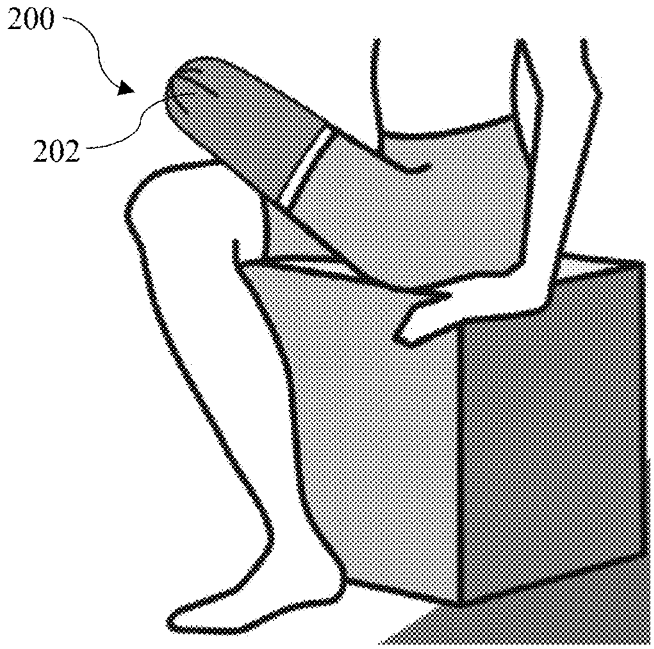
FIG. 9 is a schematic drawing showing another stage of donning of the stocking following that in FIG. 8, in which the apparatus is removed.
Figure 10:
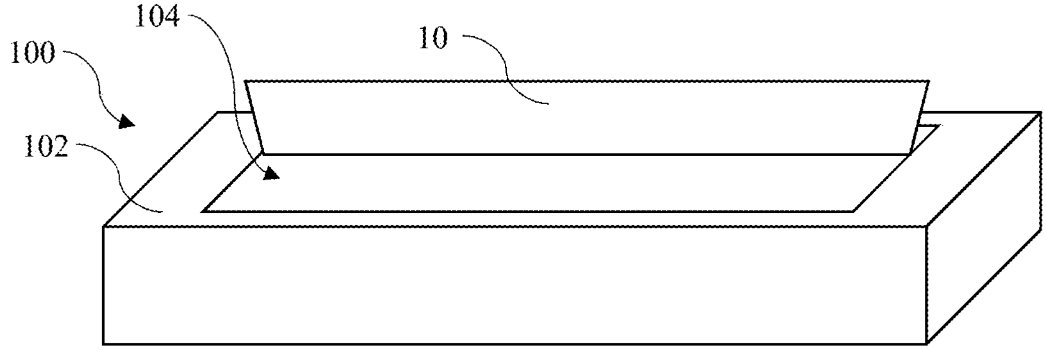
FIG. 10 is a schematic drawing of a kit comprising a plurality of apparatuses as disclosed herein.

Referring to FIGS. 7-9, a method of using the apparatus 10 can comprise pulling the sleeve 12 over a residual limb 200. For example, the sleeve 10 can be pulled to a position in which an end of the residual limb is between the first end 14 and the second end 16 of the sleeve 12. A garment, such as a stocking 202, can be pulled over the sleeve 12. The sleeve 12 can be torn along the at least one perforation 24, and the sleeve can be removed from the residual limb 200. Optionally, the sleeve 12 can be (at least partly) torn as the garment is pulled over the sleeve. That is, the steps need not be performed in sequence.

In further aspects, it is contemplated that the sleeve 12 itself can be configured to slide against the residual limb so that the garment and sleeve 12 can slide along the residual limb together. At least one of the series of perforations 24 of the sleeve 12 can permit the sleeve to split at the second end 16 to permit the sleeve 12 to slide along the residual limb. In further aspects, the user can tear the sleeve 12 along a series of perforations toward the second end 16.

A kit 100 can comprise a container 102 (e.g., a box or dispenser) and a plurality of apparatuses 10 disposed within the container. Optionally, the container 102 can comprise an opening 104 through which respective apparatuses 10 can be readily retrieved for use. It is contemplated that the kit 100 can be provided at a location where multiple disposable apparatuses for donning garments over residual limbs is desired. For example, the kit can be provided at a healthcare facility, such as those that frequently provide care for recent individuals with recent amputations. In another aspect, the kit 100 can be provided to an individual with a recent amputation. In particular, the apparatuses 10 can be advantageous for use in acute settings. For example, recent amputations can be associated with fragile skin and tissue. The disclosed apparatuses can facilitate donning of garments over the fragile skin and tissue. Further, the apparatuses can facilitate containment of biological fluids, including blood and plasma. For example, following use, the apparatuses can be disposed of, and additional apparatuses can be removed from the container 102 as needed. When all the apparatuses from a given container 102 have been used, a new, full container can be provided at the location.

In some aspects, it can be desirable to have access to different sizes of sleeves 12. For example, at medical facilities where care for individuals with recent amputations is frequently provided, it can be beneficial to have access to sleeves of different sizes that can be selected depending upon the size and anatomy of each individual in need of care. A system can comprise a plurality of apparatuses 10, wherein at least two apparatuses of the plurality of apparatuses differ in at least one dimension. For example, the system can comprise a plurality of kits, wherein each kit comprises a plurality of apparatuses of a respective different size. In some aspects, the kits can be provided in sizes, such as small, medium, and large. In further aspects, the apparatuses/kits can be sized for different locations of amputation, such as below-the-knee, at-the-knee, or above-the-knee.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. An apparatus for donning a garment over a residual limb, the apparatus comprising:
- a sleeve having a first end and a second end spaced along a longitudinal axis, wherein the sleeve has:
  - a peripheral sidewall surrounding the longitudinal axis;
  - an opening defined by the peripheral sidewall and extending continuously through the sleeve from the first end to the second end; and
  - at least one series of perforations extending from the first end to the second end of the sleeve,
- wherein the sleeve defines a taper that extends continuously from the first end to the second end.

2. The apparatus of claim 1, wherein the peripheral wall has a first edge at the first end and a second edge at the second end, wherein the first edge surrounds the opening of the sleeve at the first end, and wherein the second edge surrounds the opening at the second end.

3. The apparatus of claim 2, wherein at least a portion of the first edge defines a cutout extending toward the second end of the sleeve.

4. The apparatus of claim 1, wherein the sleeve is unitarily formed.

5. The apparatus of claim 1, wherein the sleeve has at least one longitudinal weld extending from the first end to the second end.

6. The apparatus of claim 5, wherein the at least one longitudinal weld comprises a first longitudinal weld on a first side of the sleeve and a second longitudinal weld on a second side of the sleeve.

7. The apparatus of claim 1, wherein the sleeve comprises polymer.

8. The apparatus of claim 1, wherein the sleeve comprises polyethylene.

9. The apparatus of claim 1, wherein the peripheral side wall of the sleeve has a thickness of 3 thousandths of an inch or less.

10. The apparatus of claim 1, wherein the at least one series of perforations comprises a plurality of series of perforations, wherein the respective series of perforations of the plurality of series of perforations are circumferentially spaced about an outer surface of the peripheral sidewall.

11. The apparatus of claim 10, wherein the plurality of series of perforations are evenly circumferentially spaced about the outer surface of the peripheral sidewall.

12. The apparatus of claim 1, wherein the at least one series of perforations is configured to permit tearing of the sleeve from the first end to the second end.

13. A kit comprising:
- a container; and
- a plurality of apparatuses as in claim 1 disposed within the container.

14. An apparatus for donning a garment over a residual limb, the apparatus comprising:
- a sleeve having a first end and a second end spaced along a longitudinal axis, wherein the sleeve has:
  - a peripheral sidewall surrounding the longitudinal axis;
  - an opening defined by the peripheral sidewall and extending continuously through the sleeve from the first end to the second end; and
  - at least one series of perforations extending from the first end to the second end of the sleeve,
- wherein the peripheral sidewall of the sleeve has an outer surface and an inner surface, wherein the sleeve defines at least one transverse opening extending through the peripheral sidewall of the sleeve from the outer surface to the inner surface, wherein the at least one transverse opening is sized to receive a plurality of fingers therethrough.

15. The apparatus of claim 14, wherein the at least one transverse opening is elongated along a transverse axis that is perpendicular to the longitudinal axis.

16. The apparatus of claim 14, wherein the at least one transverse opening is positioned closer to the first end of the sleeve than to the second end of the sleeve.

17. The apparatus of claim 14, wherein the at least one transverse opening has a major dimension of at least 3 inches.

18. An apparatus for donning a garment over a residual limb of a user, the apparatus comprising:
- a sleeve having a first end and a second end spaced along a longitudinal axis, wherein the sleeve has:
  - a peripheral sidewall surrounding the longitudinal axis;
  - an opening defined by the peripheral sidewall and extending continuously through the sleeve from the first end to the second end; and
  - at least one series of perforations extending from the first end to the second end of the sleeve,
- wherein at least a portion of the sleeve is configured to receive therethrough at least a portion of a thigh of the residual limb of the user having a circumference from 16 inches to 25 inches;
- wherein the apparatus is symmetric about a first plane that includes the longitudinal axis and a second plane that includes the longitudinal axis and is perpendicular to the first plane.

* * * * *